United States Patent [19]

Tufano

[11] Patent Number: 4,801,523

[45] Date of Patent: Jan. 31, 1989

[54] PROCESS FOR THE PREPARATION OF OCTAHEDRAL SILVER CHLORIDE-CONTAINING EMULSIONS

[75] Inventor: Thomas P. Tufano, Wilmington, Del.

[73] Assignee: E. I. Du Pont de Nemours and Company, Wilmington, Del.

[21] Appl. No.: 90,555

[22] Filed: Aug. 28, 1987

[51] Int. Cl.$^4$ .............................................. C03C 1/02
[52] U.S. Cl. .................................... 430/589; 430/480; 430/486; 430/613; 430/614; 430/966
[58] Field of Search ............... 430/567, 569, 966, 613, 430/614, 486, 480

[56] References Cited

U.S. PATENT DOCUMENTS

| | | | |
|---|---|---|---|
| 4,292,391 | 9/1981 | Overman | 430/267 |
| 4,469,784 | 9/1984 | Heki et al. | 430/569 |
| 4,610,958 | 9/1986 | Matsuzaka et al. | 430/569 |
| 4,636,457 | 1/1987 | Valbusa et al. | 430/375 |
| 4,695,534 | 9/1987 | Bryan et al. | 430/569 |

OTHER PUBLICATIONS

Claes, et al., "Crystal Habit Modification of AgCl by Impurities Determining the Solvation," *The Journal of Photographic Science*, vol. 21, pp. 122–124, Jun. 1973.

D. Wyrsch, "Sulfur Sensitization of Monosized Silver Chloride Emulsions with <111>, <110> and <100> Crystal Habit (FC-4)", paper III-13, International Congress of Photographic Science, pp. 122–124, 1978.

*Primary Examiner*—Mukund J. Shah

[57] ABSTRACT

Process for preparing photographic emulsion comprising bringing aqueous silver and chloride-containing halide salt solutions into contact in the presence of a dispersing medium to form octahedral silver halide grains having a halide content of at least 50 mole percent chloride, based on total moles of silver present, the improvement forming the grains in the presence of a crystal modifying amount of an aminoazapyridine as described in pH range of 2.5 to 9, pCl range of 0 to 3, the aminoazapyridine compound being added after at least about 6% to about 45% of the silver salt solution has been added.

The photographic emulsion is useful in x-ray, laser scanner films, as color separation elements and inverse transfer systems, etc.

14 Claims, 6 Drawing Sheets

F I G. 1
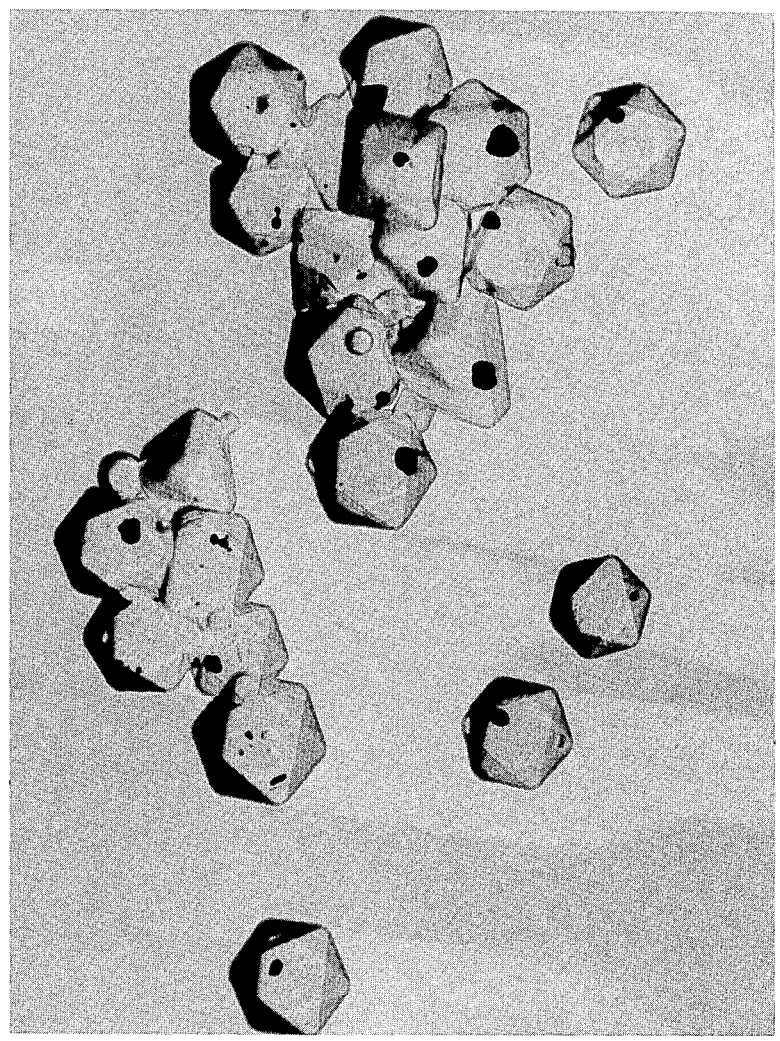
1 μm

F I G. 2
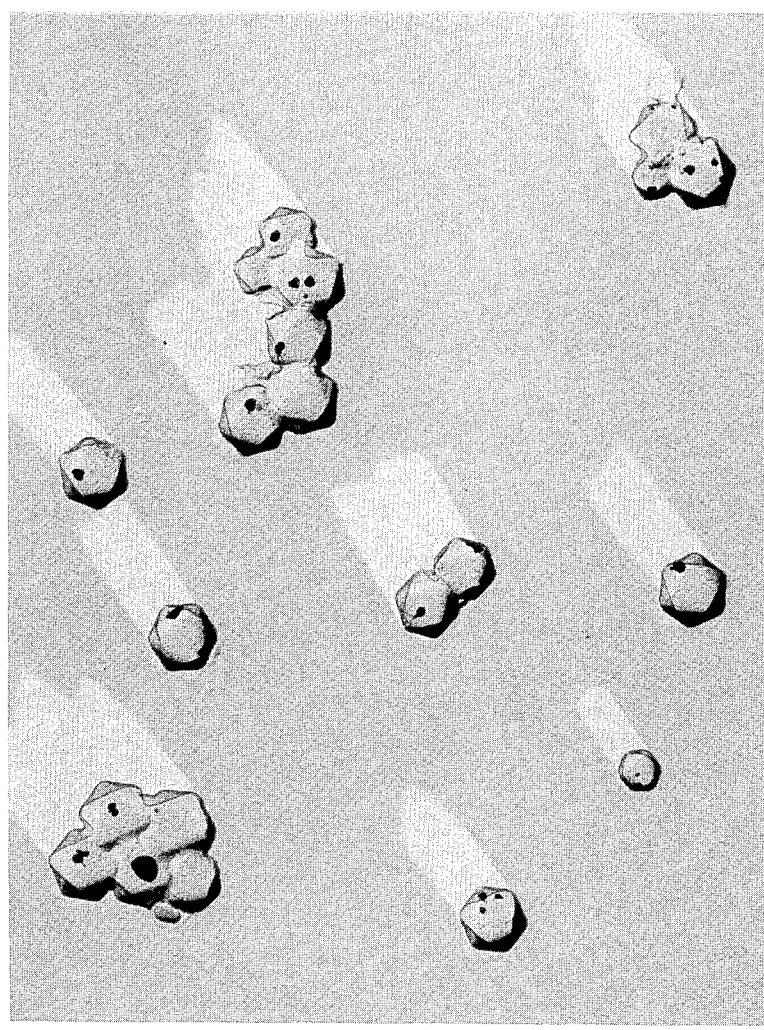
1 μm

F I G. 3
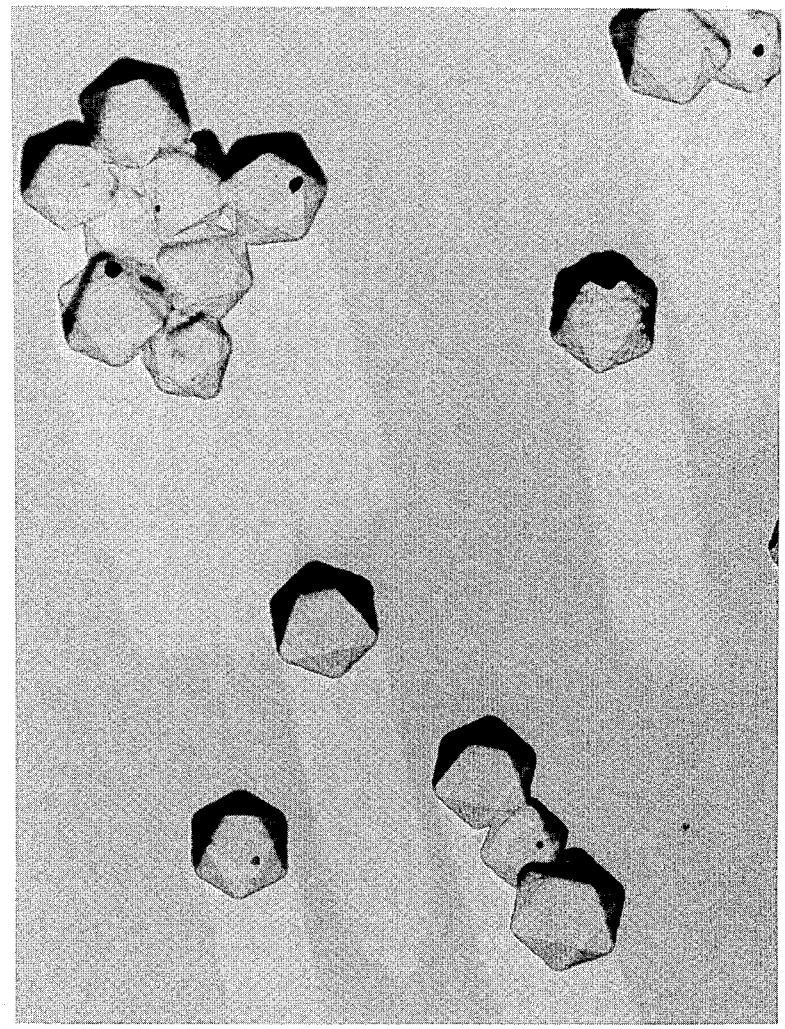
1 μm

F I G. 4
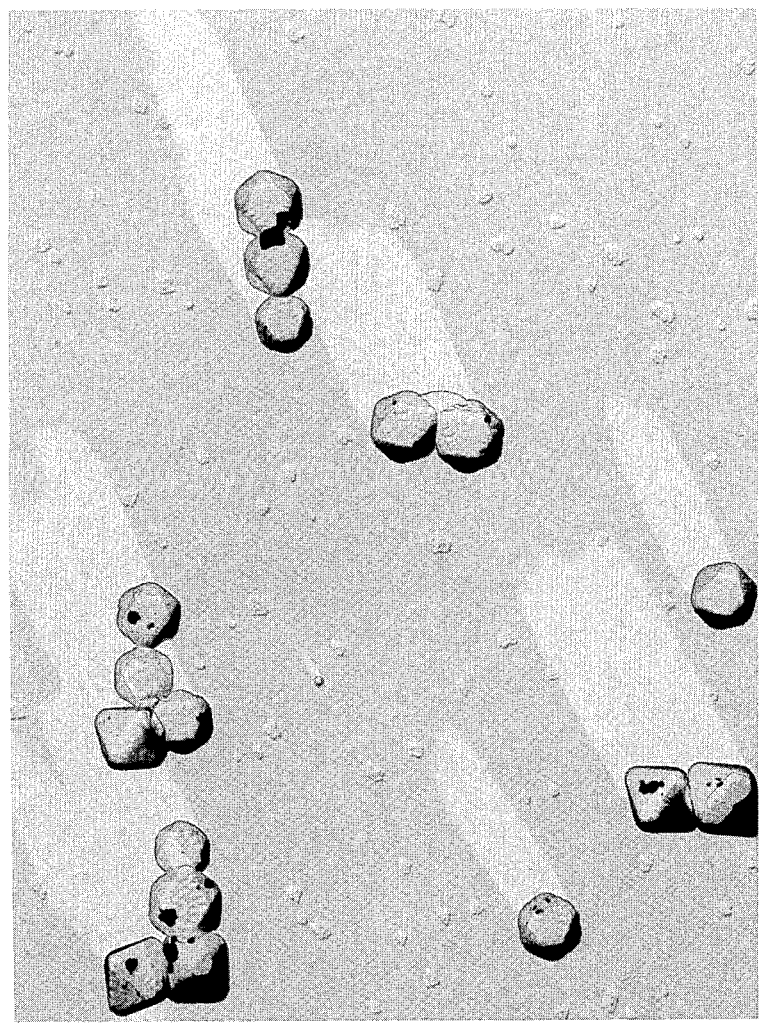
1 μm

1 μm

F I G. 6
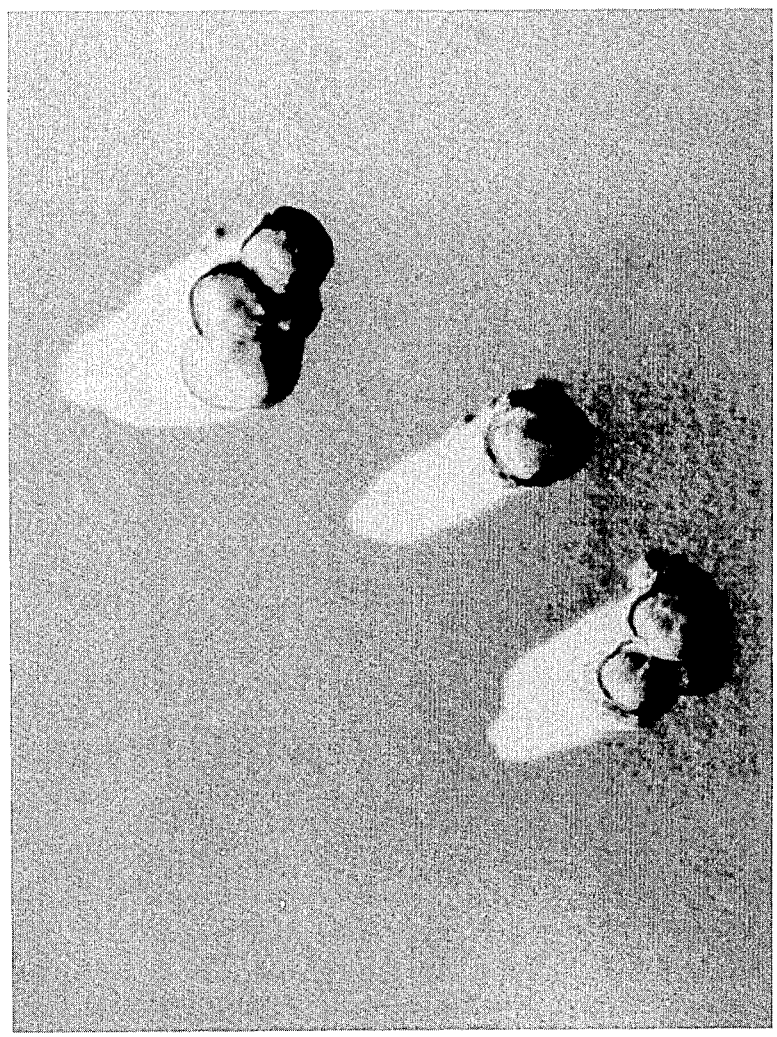
1 μm

PROCESS FOR THE PREPARATION OF OCTAHEDRAL SILVER CHLORIDE-CONTAINING EMULSIONS

FIELD OF THE INVENTION

This invention relates to a new process for the preparation of a radiation-sensitive photographic silver halide emulsion. More particularly, this invention relates to a process for the preparation of a silver halide emulsion having silver halide grains wherein at least 50% of the total grain population are octahedral in shape.

BACKGROUND OF THE INVENTION

Photographic elements made predominantly of silver chloride, with minor amounts of silver bromide and iodide (e.g., >70% chloride), are known in the prior art. These elements have wide processing latitude and can be made and utilized for most of the art fields which employ silver halide as the sensitive medium. However, since silver chloride-containing elements are much slower than those containing mainly silver bromide, the use of such elements has been generally limited to graphic arts applications, e.g., contact, low-speed camera films, etc. Since silver chloride is generally more soluble than the other silver halides, processing of exposed elements is more conveniently done. It would be desirable to use this benefit in many of the other silver halide art fields.

It is well recognized in the art that silver chloride strongly favors the formation of cubic crystals having {100} crystal faces. In the majority of photographic emulsions silver chloride crystals when present are in the form of cubic grains. With some difficulty it has been possible to modify the crystal habit of silver chloride. Claes et al, "Crystal Habit Modification of AgCl by Impurities Determining the Solvation", The Journal of Photographic Science, Vol. 21, pp. 39–50, 1973, teaches the formation of silver chloride crystals with {110} (rhombododecahedral) and {111} (octahedral) faces through the use of various grain growth modifiers. Wyrsch, "Sulfur Sensitization of Monosized Silver Chloride Emulsions with {111}, {110}, and {100} Crystal Habit", Paper III-13, International Congress of Photographic Science, pp. 122–124, 1978, discloses a triple-jet precipitation process in which silver chloride is precipitated in the presence of ammonia and small amounts of divalent cadmium ions. In the presence of these cadmium ions, control of pAg (the negative logrithim of silver ion concentration), and pH resulted in the formation of rhombododecahedral, octahedral, and cubic crystal habits, presenting grain faces lying in {110}, {111}, and {100} crystallographic planes, respectively.

It is thus apparent that the photographic art has been limited to a few methods for the preparation of useful octahedral chloride-containing emulsions. Octahedral, silver chloride-containing grains with {111} crystal surfaces are of practical importance because they present a unique surface arrangement of silver and halide ions, which in turn influences the grain surface reactions and adsorptions typically encountered in photographic applications (e.g., gold, sulfur, and dye sensitization). In addition, theory teaches that the surface structure also influences interstitial silver ion concentration and the ionic space charged layer which can have pronounced effects on photographic speed.

There is a need to prepare a suitable octahedral grain emulsion wherein the grains of the emulsion are at least 50 mole percent chloride and are photographically useful without the use of a cadmium compound and in the presence of a new and effective organic grain growth modifier compound.

SUMMARY OF THE INVENTION

In accordance with this invention there is provided a process for preparing a radiation-sensitive photographic emulsion comprising bringing aqueous silver and chloride-containing halide salt solutions into contact in the presence of a dispersing medium thereby forming silver halide grains wherein at least 50% of the total grain population are octahedral silver halide grains and wherein the halide content of the silver halide emulsion is at least 50 mole percent chloride, based on the total moles of silver present, the improvement being forming the octahedral grains at a pH in the range of 2.5 to 9 and pCl or 0 to 3 in the presence of a crystal habit modifying amount of an aminoazapyridine of the formula:

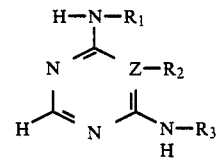

wherein Z is C or N; $R_1$, $R_2$ and $R_3$, which may be the same or different, are H or alkyl of 1 to 5 carbon atoms; when Z is C, $R_2$ and $R_3$ when taken together can be —$CH_4$=$CR_5$— or —$CH_4$=N—, wherein $R_4$ and $R_5$, which may be the same or different are H or alkyl of 1 to 5 carbon atoms, with the proviso that when $R_2$ and $R_3$ taken together is said —$CH_4$=N—, —$CH_4$= must be joined to Z; and salts thereof, with the proviso that the aminoazapyridine compound is added after at least about 6.0% to about 45% of the silver salt solution has been added.

BRIEF DESCRIPTION OF THE DRAWINGS

In the accompanying figures forming a material part of this disclosure:

FIG. 1 is a typical electron micrograph photograph (magnification 41,600) of octahedral silver iodobromochloride grains prepared according to Example 1 of this invention.

FIG. 2 is an electron micrograph photograph (magnification 20,800) of octahedral silver bromochloride grains prepared according to Example 5.

FIG. 3 is an electron micrograph photograph (magnification 41,600) of octahedral silver bromochloride grains prepared according to Example 6.

FIG. 4 is an electron micrograph photograph (magnification 25,000) of octahedral silver bromochloride grains prepared according to Example 7.

FIG. 6 is an electron micrograph photograph (magnification 38,400) of prior art irregularly-shaped silver chloride grains prepared according to Control 3.

DESCRIPTION OF PREFERRED EMBODIMENTS

Figure 5:
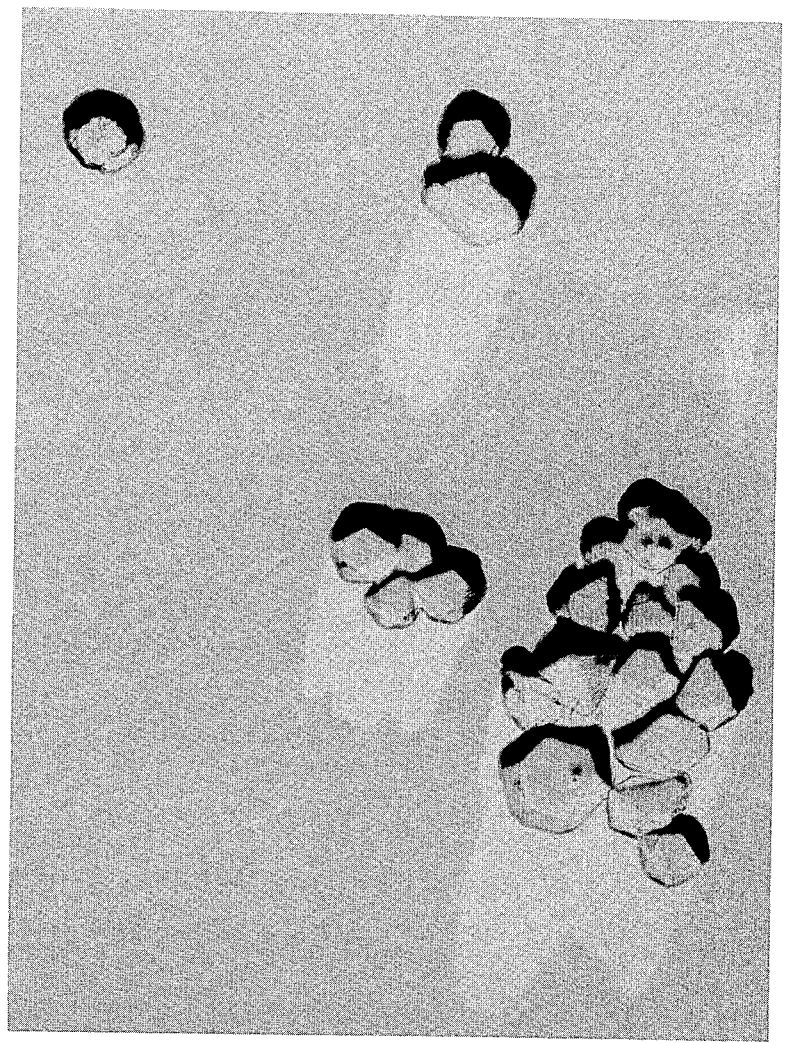
FIG. 5 is an electron microgrpah photograph (magnification 38,400) of prior art irregularly-shaped silver chloride grains prepared according to Control 2.

Throughout the specification the below-listed terms have the following meanings:

Octahedral with respect to silver chloride-containing grains means eight-sided silver chloride-containing grains whose exterior crystal faces lie in {111} crystallographic planes and are normal to axes of trigonal symmetry.

Crystal habit modifying amounts means the quantity of an aminoazapyridine compound of the invention sufficient to cause the proper octahedral grain formation.

The octahedral grain characteristics described above for the silver chloride-containing emulsions prepared by this invention can be ascertained by examining shadowed electron micrographs of these emulsions. At least 50% of the total grain population formed by this invention are octahedral in shape and preferably about 90% or greater are octahedral in shape.

In the preparation of the radiation-sensitive photographic emulsions, silver chloride-containing crystals can be prepared by standard balanced double jet (BDJ) or single-jet (SJ) procedures such as are illustrated in the examples below or as known to those skilled in the art. The emulsion's halide content is at least 50 mole percent chloride, based on the total moles of silver present. Amounts of iodide and/or bromide can be present. The mole percent bromide can range up to 49 mole % and the iodide up to 2 mole %, based on the total moles of silver. The emulsions when made by the conventional BDJ procedure utilize solutions consisting essentially of the halide salt, e.g., chloride or chloride, bromide and optionally iodide in small amount, and one containing the silver salt are added simultaneously to a solution of dispersing medium such as gelatin in a suitable mixing vessel. Conventionally, small amounts of the halide solution may also be present in the vessel. An amount, e.g., at least about 6% to about 45% by weight, preferably 10 to 30% by weight, of the silver salt solution has been added prior to the addition of the crystal habit modifying amount of aminoazapyridine compound. By controlling the pH, pCl, the time the two solutions are "jetted" into the mixing vessel, and the temperature, one can generally predict the characteristics of the octahedral silver halide grains prepared.

Alternatively, and also as is known, an SJ procedure may be used. In this procedure, illustrated in Example 8 below, all the desired halide is added to a suitable agitated reaction vessel along with the binding agent, e.g., gelatin. Seed crystals are generated, e.g., by the addition of silver nitrate solution. As described above, at least 6% to not more than 45% by weight, preferably 10 to 30% by weight of the silver salt solution is added prior to the addition of the crystal habit modifying amount of the aminoazapyridine compound. The silver salt solution may be added in steps. As with the BDJ procedures, the pH, pCl, time and temperature are selected to produce the desired grain size.

Typical aminoazapyridine compounds within the scope of the formula set out above include, but are not limited to: 4-aminopyrazolo[3,4,d]pyrimidine, 4,6-diaminopyrimidine hemisulfate monohydrate, 2,4-diamino-1,3,5-triazine, 4,6-bis(methylamino)-pyrimidine, etc. In general the amount of aminoazapyridine compound present ranges from 0.0001 to 1.0 mole percent, preferably 0.05 to 0.5 mole percent, based on the total moles of silver halide formed. The aminoazapyridine compounds generally can be dissolved in water or other suitable solvent, e.g., lower alcohols such as methanol, ethanol, etc., which are compatible with the process for making photographic emulsions, and added to the reaction vessel after the seeding phase of the precipitation of the emulsion grains as described above. It is believed that some tabular crystals may be formed if the aminoazapyridine compound is added prior to or during the seeding phase of the precipitation, e.g., prior to about 6 percent of the silver salt solution being added. Cubo-octahedral and/or cubic grains may be formed if the aminoazapyridine compound is added after about 45 percent of the silver salt solution has been added. Small amounts of other adjuvants to assist int he solubilization of these ocmpounds may also be present.

The emulsions of this invention can be used in any of the conventional photographic systems, e.g. negative or positive-working systems. Thus, they can contain any of the adjuvants related to the particular system employed. For example, the emulsions, when employed as direct positives, may be chemically fogged using agents such as boranes, optimally in the presence of gold salts. The emulsions may contain small amounts of metal ion dopants such as rhodium, iridium, and the like, and appropriate dyes to control contrast and spectral sensitivity, for example.

Th octahedral, mainly silver chloride, grains of this invention are preferably grown in the presence of a dispersing agent such as gelatin, though other natural or synthetic binding materials, e.g., phthalated gelatin, etc., may also be used alone or mixed with gelatin. After the octahedral grains of this invention are made, they may then be suitably dispersed in larger amounts of binder, e.g., gelatin, and coated on any of the conventional photographic supports. Paper and particularly film supports such as those made of polyethylene terephthalate suitably subbed as described by Alles, U.S. Pat. No. 2,779,689, Example IV, are preferred, though any other conventional photographic support described in the prior art can be used within the ambit of this invention, as well-known to those skilled in the art. Filter dyes may also be present to removew unwanted light. Emulsions containing the grains of this invention may also contain other well-known adjuvants such as hardeners, wetting agents, antifoggants, antihalation layers, and coating aids, among others. Procedures described in Research Disclosure of Product Licensing Index, December 1971, page 107 are applicable also to the emulsions of this invention, the disclosure of which is incorporated herein. A preferred mode of the invention is found in Examples 1 and 2 below.

INDUSTRIAL APPLICABILITY

The emulsions of this invention can be used to prepare photographic film elements in any of the conventional areas. These films can be used, for example, in the field of X-ray, as color separation elements, as laser scanner films, inverse transfer systems, or in "dry-silver" applications. When properly sensitized and treated with color-forming agents in the conventional and well-known manner, films useful as color negatives or positives can be made with the octahedral grains of this invention.

EXAMPLES

The examples illustrate but do not limit the invention and the percentages set forth therein are by weight.

EXAMPLE 1

The following ingredients were placed in a suitable reaction vessel:

| Ingredient | Amount |
| --- | --- |
| 10% Aqueous Gelatin | 80.0 grams |
| KCl | 4.850 grams |
| 3 M KBr solution | 0.1 mL |
| 2.0 mM RhCl$_3$ solution | 0.063 mL |
| Deionized H$_2$O | 420.0 mL |

The pH was adjusted to 4.0 with 1.5M sulfuric acid, and the above ingredients were stirred and heated to 60° C. In separate vessels, aqueous solutions of 3.0M AgNO$_3$(-the silver salt solution), and a mixture of 3.0M KCl, 3.0M KBr and solid KI (20% Br, 0.1% I: the halide salt solution) were prepared. A pump was used to meter each of these solutions into the reaction vessel. Seed crystals were formed by "single-jetting" the above silver salt solution at 1.8 mL/minute until the chloride ion concentration in the reaction vessel was reduced to 0.05M. At this point, both the silver and halide solutions were "double-jetted" into the reaction vessel to maintain the pCl at 1.3. At t=8 minutes (14.4% silver added), the silver and halide addition was halted. A solution of 0.12 g of 4-aminopyrazolo[3,4,d]pyrimidine in 50 mL H$_2$O (solution acidified with 1.5M sulfuric acid to facilitate dissolution of the pyrimidine compound) was added to the reaction vessel. The pH of the reaction mixture was re-adjusted to 4.0, as required. At t=10 minutes, silver and halide addition were resumed. After 18% of the silver solution had been added, the silver flow rate was increased to ca. 1.5× the initial seeding level, and the halide flow rate was adjusted to maintain the constant pCl of 1.3. This was maintained until 100 mL of the silver solution had been added (0.3 mole Ag). The resultant AgCl$_{75.8}$Br$_{24.1}$I$_{0.1}$ grains were examined by a replica technique in an electron microscope to determine grain shape. An electrolytic grain size analyzer (EGSA) was used to determine grain volume. The attached electron micrograph photograph (FIG. 1) shows excellent octahedral grains were formed with a median volume-weighted grain volume of 0.026 $\mu$m$^3$.

EXAMPLE 2

The following ingredients were placed in a reaction vessel similar to that used in Example 1.

| Ingredient | Amount |
| --- | --- |
| 10% Aqueous Gelatin | 60.0 grams |
| NH$_4$Cl | 2.0 grams |
| 3 M NH$_4$Br | 0.25 mL |
| Deionized water | 240.0 mL |

The pH was adjusted to 4.0 with 1.5M sulfuric acid, and the above ingredients were stirred and heated to 60° C. Other additions and procedures were the same as described above in Example 1 with the following modifications. The halide salt solution was a mixture of 3.0M KCl and 3.0M KBr (1% Br). The silver seeding and growth flow rates were 1 and 2 mL/minute, respectively. 0.04 g of 4-aminopyrazolo[3,4,d]pyrimidine in 20 mL H$_2$O was added after 10% of the silver solution had been added. A total of 0.15 mole of emulsion with the composition AgCl$_{98.5}$Br$_{1.5}$ was precipitated in ca. 28 minutes. Excellent octahedral grains were produced with a median volume of 0.033 $\mu$m$^3$.

EXAMPLE 3

The following ingredients were placed in the reaction vessel of Example 1:

| Ingredient | Amount |
| --- | --- |
| 10% Aqueous Gelatin | 80.0 grams |
| KCl | 4.85 grams |
| 3.0 M KBr | 0.5 mL |
| Deionized H$_2$O | 420.0 mL |

The pH was adjusted to 4.0 with 1.5M sulfuric acid, and the above ingredients were stirred and heated to 60° C. Other additions and procedures were the same as described in Example 1 except that the halide salt solution was a 10% mixture of 3.0M KBr in 3.0M KCl. An excellent ApCl$_{90}$Br$_{10}$ emulsion with median grain volume of 0.007 $\mu$m$^3$ resulted from this preparation.

EXAMPLE 4

The following ingredients were placed in the reaction vessel of Example 1:

| Ingredient | Amount |
| --- | --- |
| 10% Aqueous Gelatin | 80.0 grams |
| KCl | 4.85 grams |
| Deionized H$_2$O | 420.0 mL |

The additions and procedures were identical to those described for Example 1 except that the halide salt solution was solely a 3.0M KCl solution. Consistent with the findings for the above examples, well-formed octahedral grains with median volume, 0.021 $\mu$m$^3$, were produced in this preparation.

EXAMPLE 5

The ingredients and procedures were similar to those described in Example 1 with the following modifications: The pH of the reaction mixture was maintained at 7.0 throughout the precipitation. The halide salt solution was a 2% mixture of 3.0M KBr in 3.0M KCl. 0.16 g of 4,6-dimaminopyrimidine hemisulfate monohydrate dissolved in warm H$_2$O was used to precipitate 0.3 mole of octahedral emulsion grains. The median grain volume, as measured on the EGSA, is 0.036 $\mu$m$^3$. The attached electron micrograph photograph (FIG. 2) shows the replicated crystals produced.

EXAMPLE 6

The ingredients and procedures are the same as described in Example 5, but the pH in this experiment was controlled at 5.0, and 0.10 g of 2,4-diamino-1,3,5-triazine was used to produce the AgCl$_{98}$Br$_2$ microcrystals shown in the attached electron micrograph photograph (FIG. 3). The median grain volume was 0.024 $\mu$m$^3$.

EXAMPLE 7

The ingredients and procedures were the same as described in Exmaple 5, except that 0.042 g of 4,6-bis(-methylamino)pyrimidine was used to promote the growth of octahedral AgCl$_{97.9}$Br$_{2.1}$ microcrystals with median grain volume of 0.029 $\mu$m$^3$. The attached electron micrograph photograph (FIG. 4) shows replicas of the octahedral grains obtained.

EXAMPLE 8

The following ingredients were placed in a reaction vessel:

| Ingredient | Amount |
|---|---|
| 10% Aqueous Gelatin | 80.0 grams |
| KCl | 26.1 grams |
| 3 M KBr | 0.5 mL |
| Deionized H$_2$O | 420.0 mL |

The pH was adjusted to 4.0 with 1.5M sulfuric acid and the temperature to 60° C. with agitation. At this point, seed crystals were generated by adding a 3M silver nitrate solution at 1.8 mL/minute. After 19.8% of the silver solution had been added, the addition was halted. 0.08 g of 4-aminopyrazolo[3,4,d]pyrimidine dissolved in 50 mL H$_2$O (made acidic with sulfuric acid as described in Example 1) was added. After 2 minutes, the silver addition was continued. When 21.6% silver solution had been added, the silver flow rate was increased to ca. 2× the initial seeding level. Silver addition continued in this "single-jet" fashion until 100 mL of the silver solution had been added (0.3 mole AgX precipitated). As in Example 1, the pH was controlled at 4.0 with 3M aqueous NaOH throughout the precipitation. Electron microscopy indicated that emulsion crystals with excellent octahedral features were formed using this process. Particle size analysis indicated that the median grain volume was 0.44 μm$^3$.

EXAMPLE 9

In a reaction vessel similar to that used in Example 1, the following ingredients were placed:

| Ingredient | Amount |
|---|---|
| Gelatin (Rousselot Co.) | 40.0 grams |
| KCl | 14.5 grams |
| 3 M KBr | 0.5 mL |
| Deionized H$_2$O | 1500 mL |

The reaction mixture was heated to 60° C. with agitation, and the pH was adjusted to 4.0 with 1.5M sulfuric acid. The procedures used to precipitate 1.5 moles of this iodobromochloride emulsion were analogous to thos described in Example 1. The resultant emulsion crystals were examined to determine particle size and shape. Very regular octahedral microcrystals with a median volume of 0.042 μm$^3$ were formed.

The grains were coagulated (herein called curds) at low pH (2.8–3.0), and washed several times with deionized water. The curds were mixed in water and bulk gelatin at ca. 42° C. and pH 6.0 for 45 minutes to redisperse the grains therein. Six portions of the redispersed material were sensitized (50° C. for 40 minutes) as indicated in Table 1 below and coated on a conventional polyethylene terephthalate film support that was coated, e.g., ca. 40 mg/dm$^2$ with a conventional resin sub and over which has been applied a gelatin sub layer. Each coating was dried and given a 10$^{-2}$ flash exposure through a $\sqrt{2}$ stepwedge on an EGG sensitometer. The exposed smaples were then devleoped for 90 seconds at 28° C. in a standard mixed developer (hydroquinone/phenidone), followed by 10 seconds in a conventional acid stop bath and 60 seconds in a conventional sodium thiosulfate fixer. The samples were then rinsed in water and dried. The following results were obtained:

TABLE 1

| Portion | Sensitization Technique | D$_{min}$ | Relative Speed[a] |
|---|---|---|---|
| 1 | No Sensitizers | 0.06 | 100 |
| 2 | Dye 1 only[b] | 0.04 | 500 |
| 3 | Dye 2 only[c] | 0.06 | 430 |
| 4 | Au + S, only | 0.03 | 800 |
| 5 | Dye 1, Au + S | 0.06 | 8600 |
| 6 | Dye 2, Au + S | 0.05 | 2700 |

[a]As measured at 0.10 density above base plus fog.
[b]A conventional orthochromatic carbocyanine dye.
[c]A conventional blue-absorbing merocyanine dye.

The data given above clearly indicate that octahedral high-chloride emulsions prepared by the process of this invention can be chemically and spectrally sensitized, coated and processed using conventional techniques, common to those skilled in the art.

CONTROL 1

The following ingredients were placed in a reaction vessel similar to that used in Example 1.

| Ingredient | Amount (g) |
|---|---|
| 10% Aqueous Gelatin | 400.0 |
| NH$_4$Cl | 17.6 |
| NH$_4$Br | 0.73 |
| Deionized water | 1600.0 mL |

The pH was adjusted to 4.0 with 1.5M sulfuric acid, and the above ingredients were stirred and heated to 40° C. Other additions and procedures were the same as described in Example 1 with the following modifications: The halide salt solution was a mixture of 3.0M NH$_4$Cl and 3.0M NH$_4$Br (2% Br). The silver seeding and growth flow rates were 10 and 20 mL/minute, respectively. No growth modifier compound was added to the reaction vessel. A total of 1.5 moles of emulsion was precipitated in ca. 32 minutes having the composition AgCl$_{97.7}$Br$_{2.3}$. Examination of the resultant bromochloride emulsion using optical and transmission electron microscopy showed that cubic microcrystals had been formed with a median grain volume of 0.0073 μm$^3$.

CONTROL 2

The following ingredients were placed in a reaction vessel similar to that used in Example 1.

| Ingredient | Amount (g) |
|---|---|
| Gelatin (Rousselot Co.) | 10.0 |
| KCl | 2.61 |
| Deionized H$_2$O | 1000.0 mL |

The pH was adjusted to 5.8 with 3.0M aqueous sodium hydroxide solution, and the above ingredients were stirred and heated to 60° C. In separate vessels, aqueous solutions of 1.5M AgNO$_3$ and 1.5M KCl were prepared. Seed crystals were formed by "double-jetting" the silver and halide salt solutions into the reaction vessel at 20 mL/minute. The halide salt solution flow rate was adjusted so as to maintain a constant chloride concentration of 0.035M in the reaction vessel. After 48% of the silver solution had been added (0.42 mole; ca. 60 grams AgCl precipitated), the silver and halide solution addition was stopped. 2.0 grams of thiourea (growth modifying compound of prior art) was added to the reaction vessel, and after ca. 2 minutes, silver and halide solution addition was resumed at the same respective flow rates. Precipitation continued until 0.87 mole of silver chloride was formed. The attached electron micrograph photograph (FIG. 5) shows the replicated crystals produced as being irregularly formed with only slight octahedral growth tendencies.

CONTROL 3

The ingredients and procedures were the same as described in Control 2 with the exception that 2.0 grams of adenine (in place of thiourea) was added to the precipitation vessel after 48% of the silver salt solution had been added. The attached electron micrograph photograph (FIG. 6) shows the grains produced as being poorly-formed and irregular in shape with only slight octahedral growth tendencies.

I claim:

1. A process for preparing a radiation-sensitive photographic emulsion comprising bringing aqueous silver and chloride-containing halide salt solutions into contact in the presence of a dispersing medium thereby forming silver halide grains wherein at least 50% of the total grain population are octahedral silver halide grains and wherein the halide content of the silver halide emulsion is at least 50 mole percent chloride, based on the total moles of silver present, the improvement being forming the octahedral grains at a pH in the range of 2.5 to 9 and a pCl of 0 to 3 in the presence of a crystal habit modifying amount of an organic nitrogen-containing heterocyclic compound of the formula:

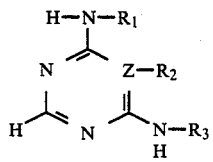

wherein Z is C or N; $R_1$, $R_2$ and $R_3$, which may be the same or different, are H or alkyl of 1 to 5 carbon atoms; when Z is C, $R_2$ and $R_3$ when taken together can be —$CR_4$=$CR_5$— or —$CR_4$=N—, wherein $R_4$ and $R_5$, which may be the same or different are H or alkyl of 1 to 5 carbon atoms, with the proviso that when $R_2$ and $R_3$ taken together is said —$CR_4$=N—, —$CR_4$= must be joined to Z; and salts thereof, with the proviso that the organic nitrogen-containing heterocyclic compound is added after at least about 6.0% to about 45% of the silver salt solution has been added.

2. A process according to claim 1 wherein $R_1$, $R_2$, $R_3$, $R_4$, and $R_5$ which may be the same or different, are H or alkyl of 1 to 2 carbon atoms.

3. A process according to claim 1 wherein the organic nitrogen-containing hetercyclic compound is 4-aminopyrazolo-[3,4,d]pyrimidine.

4. A process according to claim 1 wherein the organic nitrogen-containing hetercyclic compound is 4,6-diaminopyrimidine hemisulfate monohydrate.

5. A process according to claim 1 wherein the organic nitrogen-containing hetercyclic compound is 2,4-diamino-1,3,5-triazine.

6. A process according to claim 1 wherein the organic nitrogen-containing hetercyclic compound is 4,6-bis(methylamino)-pyrimidine.

7. A process according to claim 1 wherein the organic nitrogen-containing hetercyclic compound is present in an amount of 0.0001 to 1.0 mole percent based on the total moles of silver halide formed.

8. A process according to claim 1 wherein the organic nitrogen-containing heterocyclic compound is present in an amount of 0.05 to 0.5 mole percent based on the total moles of silver halide formed.

9. A process according to claim 1 wherein the dispersing medium is galatin.

10. A process according to claim 1 wherein the silver halide emulsion is a silver chloride emulsion 11. A process according to claim 1 wherein the sivler halide emulsion is a silver bromochloride emulsion, the bromide constituent being present in a maximum amount of 49 mole percent.

12. A process according to claim 1 wherein the silver halide emulsion is a silver iodobromochloride emulsion, the bromide and iodide constituents being present in a maximum amount of 48 and 2 mole percent, respectively.

13. A process according to claim 1 wherein the octahedral grains are formed at a pCl of 0.3 to 1.7 and a pH in the range of 3.5 to 8.0.

14. A process according to claim 1 wherein of the total formed grain population at least 90% are octahedral silver halide grains.

* * * * *